(12) United States Patent
Hirota

(10) Patent No.: US 6,521,794 B2
(45) Date of Patent: Feb. 18, 2003

(54) METHOD FOR PRODUCTION OF AROMATIC COMPOUNDS

(75) Inventor: Kouichi Hirota, Kobe (JP)

(73) Assignee: Nippon Shokubai Co., Ltd. (JP)

(*) Notice: Subject to any disclaimer, the term of this patent is extended or adjusted under 35 U.S.C. 154(b) by 0 days.

(21) Appl. No.: 10/062,007

(22) Filed: Feb. 1, 2002

(65) Prior Publication Data
US 2002/0156322 A1 Oct. 24, 2002

(30) Foreign Application Priority Data

Feb. 2, 2001 (JP) ........................................ 2001-026460
Jul. 12, 2001 (JP) ........................................ 2001-211549

(51) Int. Cl.$^7$ .............................................. C07C 21/00
(52) U.S. Cl. ...................... 564/442; 564/441; 564/124; 564/129; 560/456
(58) Field of Search ................................ 564/442, 441, 564/124, 129; 562/456

(56) References Cited

FOREIGN PATENT DOCUMENTS

| EP | A-0 415 595 | 3/1991 |
|---|---|---|
| EP | A-0 497 213 | 8/1992 |
| JP | A-06-211756 | 8/1994 |
| JP | A-8-2689979 | 3/1995 |
| JP | A-08-268979 | 10/1996 |

*Primary Examiner*—Samuel Barts
(74) *Attorney, Agent, or Firm*—Mathews, Collins, Shepherd & McKay, P.A.

(57) ABSTRACT

For the production of an aromatic compound by hydrolyzing and decarboxylating a corresponding aromatic cyano compound in the presence of an acidic substance, this invention provides a method for the production of the aromaic compound, characterized by carrying out the reactions of hydrolysis and decarboxylaion in multiple steps. Particularly when the aromatic cyano compound contains a halogen, this method effectively prevents the reaction vessels from being corroded by the by-produced hydrogen halogenide and enables the target compound to be produced in a high yield.

17 Claims, No Drawings

METHOD FOR PRODUCTION OF AROMATIC COMPOUNDS

BACKGROUND OF THE INVENTION

1. Field of the Invention

This invention relates to a method for the production of aromatic compounds and more particularly to a method for the production of aromatic compounds by using a halogen-containing aromatic cyano compound as a raw material, performing hydrolysis and decarboxylation on the raw material without inducing corrosion of the reaction vessel to obtain a corresponding aromatic compound aimed at with a high yield.

2. Description of Related Art

The tetrahalogenoanilines include important compounds which are used as intermediate raw materials for pharmaceutical preparations and agricultural pesticides. Methods for producing 2,3,5,6-tetrafluoroaniline are described in the official gazettes of JP-A-06-211,756 and JP-A-08-268,979, for example. The method described in the official gazette of JP-A-06-211,756 is claimed to obtain 2,3,5,6-tetrafluoroaniline by using a pentafluorobenzoic acid as a raw material and causing it to react with ammonia in an aqueous medium and consequently undergo amination and decarboxylation. It is described that the pentafluorobenzoic acid as the raw material can be obtained by hydrolyzing pentafluorobenzonitrile in an aqueous sulfuric acid solution and that though the aqueous reaction solution contains excess sulfuric acid and ammonium sulfate as a reaction product besides the pentafluorobenzoic acid, the obtained pentafluorobenzoic acid can be used directly in its unmodified form without being washed with water in the reaction for the production of 2,3,5,6-tetrafluoroaniline.

Then, the method disclosed in the official gazette of JP-A-08-268,979 is claimed to obtain 2,3,5,6-tetrafluoroaniline by using 4-amino-2,3,5,6-tetrafluorobenzonitrile as a raw material, adding it together with water to an aqueous sulfuric acid solution thereby enabling the 2,3,5,6-tetrafluoroaniline formed consequently by hydrolysis and decarboxylation to be distilled with water by azeotropic distillation and meanwhile causing the reaction of hydrolysis and decarboylation to proceed. Since the hydrofluoric acid which is formed by a secondary reaction corrodes reaction devices made of stainless steel or lined with glass, this method immediately distills the formed 2,3,5,6-tetrafluoroaniline azeotropically with water and feeds water to the reaction vessel for the purpose of keeping the concentration of sulfuric acid therein at a fixed level, with the result that the reaction a vessel is prevented from corrosion and the 2,3,5,6-tetrafluoroaline is obtained in a high yield.

Generally, when a given reaction involves use of sulfuric acid, for example, the reaction vessel for this reaction is made of glass or lined with glass because the vessel would be destined to incur corrosion if it was made of iron or steel. The method disclosed in the aforementioned official gazette of JP-A-08-268,979 is directed at preventing a reaction vessel from corrosion, when the method uses 4-amino-2,3,5,6-tetrafluorobenzonitrile in a low purity as a raw material, however, the vessel undergoes discernible corrosion. When the raw material is subjected to a treatment for removal of impurities in advance, the treatment would be capable of preventing the vessel from corrosion but suffer disadvantage in adding to the number of steps for the process.

In a working example cited in the official gazette of JP-A-08-268,979, the 2,3,5,6-tetrafluoroaniline is reported to be obtained in a yield of 82.5%. Thus, the desirability of further enhancing. the yield finds readily approval.

SUMMARY OF THE INVENTION

The present inventor, as a result of a detailed study on a path of synthesis of an aromatic amino compound obtained by the hydrolysis and decarboxylation of a halogen-containing aromatic cyano compounds and on a secondary product formed in the synthesis, has found that the occurrence of impurities can be repressed, the yield of the product can be enhanced, and the corrosion of a reaction vessel can be prevented by carrying out the reaction of hydrolysis and decarboxylation as divided into two discrete steps in using different conditions. As a result of further continuing a detailed study on the timing for effecting the distillation of the target product from the reaction system, he has discovered that the corrosion of the reaction vessel can be prevented and the target aromatic amino compound can be obtained in a high yield by performing the hydrolysis and decarboxylation in the presence of an aqueous medium thereby effecting formation of the aromatic amino compound and thereafter expelling the aromatic amino compound through azeotropic distillation with water. The present invention has been perfected based on the knowledge thus acquired. Specifically, this invention is aimed at providing the methods stated in the following items (1) to (3).

(1) In the production of an aromatic compound represented by the general formula (2) by hydrolyzing and decarboxylating an aromatic cyano compound represented by the general formula (1) in the presence of an acidic substance, a method for the production of the aromatic compound, characterized by performing the reactions of hydrolysis and decarboylation in multiple steps.

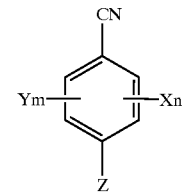

(1)

(wherein X is a halogen atom, Y is a cyano group, nitro group, or carboxyl group, Z is a nitrogen-containing group represented by —N(R$^1$)(R$^2$) (wherein R$^1$ and R$^2$ are identical or not identical substitutes superposed on a nitrogen atom and selected from among hydrogen atom and linear or branched alkyl groups of 1 to 4 carbon atoms), m is 0, 1, or 2, and n is 1, 2, 3, or 4, providing that the sum of m and n falls in the range of 1≦m+n≦4.)

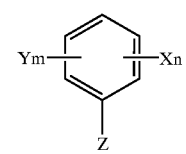

(2)

(wherein the symbols have the same meanings as in the general formula (1).)

(2) A method for the production of an aromatic compound, characterized by forming an aromatic compound represented by the general formula (2) by hydrolyzing and decarboxylating an aromatic cyano compound represented by the general formula (1) in the presence of an aqueous medium and subsequently recovering the obtained aromatic compound from the reaction solution by azeotropic distillation with water.

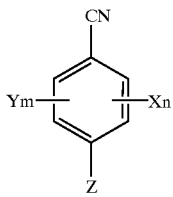

(1)

(wherein X is a halogen atom, Y is a cyano group, nitro group, or carboxyl group, Z is a nitrogen-containing group represented by —N(R¹)(R²) (wherein R¹ and R² are identical or not identical substitutes superposed on a nitrogen atom and selected from among hydrogen atom and linear or branched alkyl groups of 1 to 4 carbon atoms), m is 0, 1, or 2, and n is 1, 2, 3, or 4, providing that the sum of m and n falls in the range of $1 \leq m+n \leq 4$.)

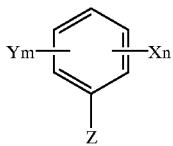

(2)

(wherein the symbols have the same meanings as in the general formula (1).)

(3) In the production of an aromatic compound represented by the general formula (2) by hydrolyzing and decarboxylating an aromatic cyano compound represented by the general formula (1) in the presence of an acidic substance, a method for the production of the aromatic compound, characterized by performing the hydrolysis and decarboxylation in multiple. steps and effecting the recovery of the formed aromatic compound from the reaction solution by azeotropic distillation with water.

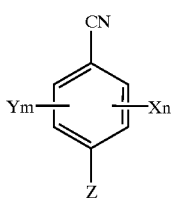

(1)

(wherein X is a halogen atom, Y is a cyano group, nitro group, or carboxyl group, Z is a nitrogen-containing group represented by —N(R¹)(R²) (wherein R¹ and R² are identical or not identical substitutes superposed on a nitrogen atom and selected from among hydrogen atom and linear or branched alkyl groups of 1 to 4 carbon atoms), m is 0, 1, or 2, and n is 1, 2, 3, or 4, providing that the sum of m and n falls in the-range of $1 \leq m+n \leq 4$.)

(2)

Ym—⟨ ⟩—Xn

Z (wherein the symbols have the same meanings as in the general formula (1).)

According to the method of this invention, by using a raw material such a halogen-containing aromatic compound as 4-amino-2,3,5,6-tetrahalogenobenzonitrile, it is made possible to produce such a corresponding aromatic compound as 2,3,5,6-tetrahalogenoaniline in a high yield. Even when the 4-amino-2,3,5,6-tetrahalogenobenzonitrile formed in low purity is hydrolyzed, decarboxylated, and azeotropically distilled particularly in the reaction vessel made of glass or lined with glass, the production of the aromatic compound can be attained in a high yield without inducing corrosion of the reaction vessel.

DETAILED DESCRIPTION OF THE PREFERRED EMBODIMENTS

The first aspect of this invention is in the production of an aromatic compound represented by the general formula (2) by hydrolyzing and decarboxylating an aromatic cyano compound represented by the general formula (1) in the presence of an acidic substance, a method for the production of the aromatic compound, characterized by performing the reactions of hydrolysis and decarboylation in multiple steps.

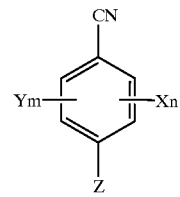

(1)

(wherein X is a halogen atom, Y is a cyano group, nitro group, or carboxyl group, Z is a nitrogen-containing group represented by —N(R¹)(R²) (wherein R¹ and R² are identical or not identical substitutes superposed on a nitrogen atom and selected from among hydrogen atom and linear or branched alkyl groups of 1 to 4 carbon atoms), m is 0, 1, or 2, and n is 1, 2, 3, or 4, providing that the sum of m and n falls in the range of $1 \leq m+n \leq 4$.)

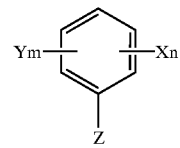

(2)

(wherein the symbols have the same meanings as in the general formula (1).)

When 4-amino-2,3,5,6-tetrafluorobenzonitrile of low purity is used as a raw material containing an aromatic cyano compound represented by the general formula (1), for example, the possibility of the reaction vessel being corroded with hydrogen fluoride will arise. By a study of the cause for this trouble, it has been found that the impurities contained in the raw material such as, for example, 2-amino-3,4,5,6-tetrafluorobenzonitrile is liable to cause such an origin of the trouble. From a further study on the relation of the trouble with corrosion, the inventor has acquired the following knowledge.

First, when 2,3,5,6-tetrafluoroaniline (F4NH) is produced by hydrolyzing and decarboxylating 4-amino-2,3,5,6-tetrafluorobenzonitrile (NFBN) with sulfuric acid, the reaction of hydrolysis and the reaction of decarboxylation are thought to proceed through a reaction process A which is composed of such steps (1) to (3) as shown below.

If the raw material compound to be used has low purity, however, the reaction process mentioned above is liable to by-produce hydrogen fluoride and induce the reaction vessel made of glass or lined with glass to succumb to corrosion. The inventor's attention has been turned particularly to 2-amino-3,4,5,6-tetrafluorobenzonitrile (o-AFBN) among other impurities contained in the raw material compound. Where the impurity compound is contained in the raw material, the process of the reactions of hydrolysis and decarboxylation permits the occurrence of the reaction process B which is formed of the following steps (5) to (7) or the occurrence of the reaction through the step (8).

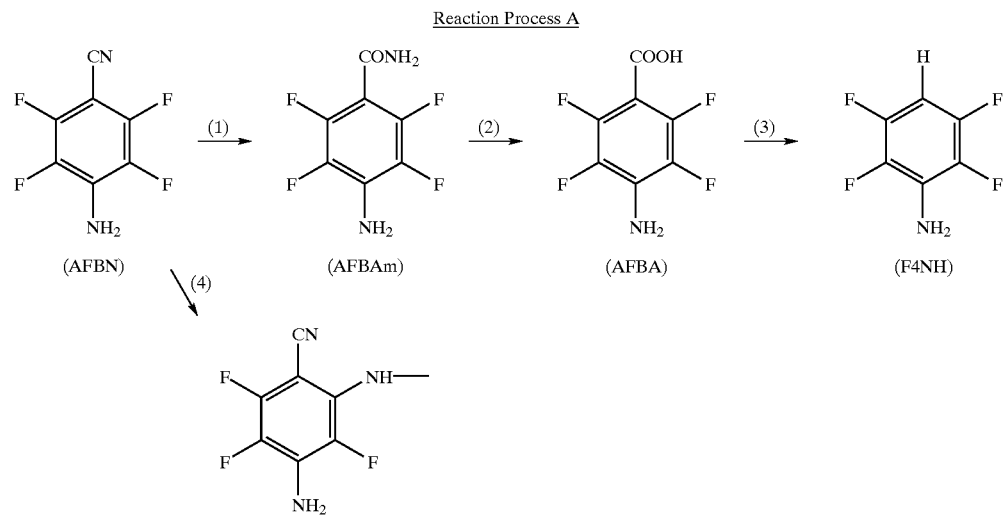

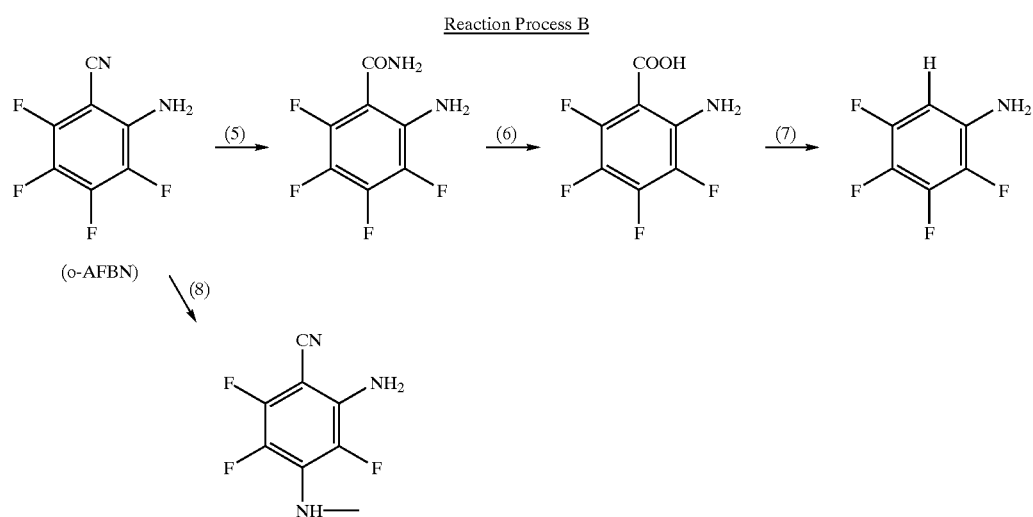

When the step (8) is passed, the substitution reaction occurring between the amino group of the target compound, 2,3,5,6-tetrafluoroaniline (F4NH), and the fluorine atom at the 4 position of 2-amino-3,4,5,6-tetrafluorobenzonitrile (o-AFBN) forms a compound represented by the following formula (3) and, at the same time, by-produces hydrogen fluoride.

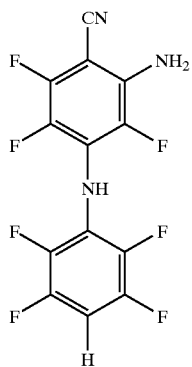

(3)

When the raw material 4-amino-2,3,5,6-tetrafluorobenzonitrile (AFBN) passes the step (4) as a secondary reaction in the reaction process A, the relevant reaction forms a compound represented by the following formula (4) mentioned below and, at the same time, by-produces hydrogen fluoride. For, the step (4) causes the fluorine atom located at the ortho position of the cyano group of the raw material AFBN to react with the F4NH compound obtained at the step (3) to produce a compound represented by the following formula (4) and, at the same time, by-produce hydrogen fluoride. The speed of this secondary reaction is estimated to be greater in the step (8) than in the step (4). To be specific, the corrosion of the reaction vessel with the by-produced hydrogen fluoride gains in prominence as the impurities in the raw material grow in concentration.

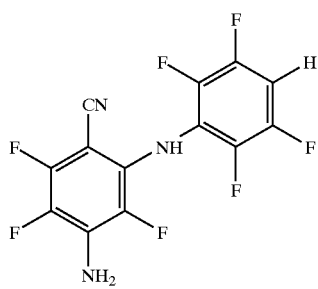

(4)

Besides the elucidation described above, it has been found that when the process of hydrolysis and decarboxylation is performed in one step in the presence of an acidic substance under the condition using an aqueous sulfuric acid solution of a concentration of 80 weight %, for example, the reactions of the step (1) and the step (5) proceed much faster than the reactions of the step (4) and the step (8) and that the reactivity with fluorine atoms is degraded because the amino group forms a sulfate under the condition. As a result, the secondary production of hydrogen fluoride is repressed and the corrosion of the reaction vessel is effectively prevented.

To continue the explanation, the compound to be formed through the steps (4) and (8) in the reaction processes A and B mentioned above possibly assumes a structure other than the structures of the compounds represented by the formulas (3) and (4) mentioned above, depending on the form of the substitution reaction.

The structures depicted at the leading ends of the paths (4) and (8) of the reaction processes A and B mentioned above are partial structures of the compounds represented by the formulas (3) and (4) mentioned above.

It has been further found that the secondary production of hydrogen fluoride is repressed to a greater extent by performing the aforementioned reactions of hydrolysis and decarboxylation as divided in at least two steps using different conditions instead of completing them in one step. Specifically, in the multiple stages which are divided into a former step and a latter step, it is made possible to attain more effective prevention of the reaction vessel from corrosion by causing the reaction of 4-amino-2,3,5,6-tetrafluorobenzonitrile (AFBN) to proceed till the conversion ratio exceeds about 40 mol % and performing this reaction under such conditions that the product thereof has 4-amino-2,3,5,6-tetrafluorobenzamide (AFBAm) as a main component thereof and consequently enabling the conversion ratio of 4-amino-2,3,5,6-tetrafluorobenzonitrile (AFBN) to exceed 40 mol %, preferably 60 mol %, and more preferably 80 mol % while repressing the formation of 2,3,5,6-tetrafluoroaniline (F4NH) in the former step (former step reactions) and completing the hydrolysis and the decarboxylation in the latter step or thereafter.

This more effective prevention of the corrosion may be logically explained by a postulate that though the conversion ratio of 2-amino-3,4,5,6-tetrafluorobenzonitrile (o-AFBN) reaches nearly the same level, the chance of contact of o-AFBN with the target product, 2,3,5,6-tetrafluoroaniline (F4NH), is allayed or the chance of contact of the o-AFBN with the raw material, 4-amino-2,3,5,6-tetrafluorobenzonitrile (AFBN) is allayed, with the result that the formation of the compound represented by the formula (3) or the formula (4) mentioned above is repressed, and at the same time that the formation of hydrogen fluoride is repressed. Incidentally, the compound represented by the formula (3) or the formula (4) mentioned above is merely intended as an example for illustrating the relation between the presence of impurities and the occurrence of corrosion. This invention is not limited to the presence of this compound and to the repression of the formation thereof. This invention will be described in detail below.

The aromatic cyano compound represented by the general formula (1) which is used in this invention is such that in the general formula (1), the symbol Z denotes a nitrogen-containing group represented by the formula —N($R^1$) ($R^2$) (wherein $R^1$ and $R^2$ are identical or not identical substitutes superposed on a nitrogen atom and selected from among hydrogen atom and linear or branched alkyl groups of 1 to 4 carbon atoms). As concrete examples of the nitrogen-containing group, amino group, monomethyl amino group, dimethyl amino group, monoethyl amino group, diethyl amino group, monopropyl amino group, and dipropyl amino group may be cited. Among them, the amino group proves particularly suitable. The symbol Y denotes a cyano group, nitro group, or caraboxyl group, the cyano group being preferable. The halogen atom denoted by the symbol X is a fluorine atom, chlorine atom, or bromine atom, the fluorine atom being preferable. In the occurrence of a plurality of X's, the atoms denoted thereby may be identical or not identical with one another.

As concrete examples of the aromatic cyano compound represented by the general formula (1), 4-amino-2,3,5,6-tetrahalogenobenzonitrile, 4-monomethylamino-2,3,5,6-tetrahalogenobenzonitrile, 4-dimethylamino-2,3,5,6-tetrahalogenobenzonitrile, 4-amino-3,5,6-trihalogenophthalonitrile, 4-monomethylamino-3,5,6-trihalogenophthalonitrile, and 4-dimethylamino-3,5,6-trihalogenophthalonitrile may be cited. Among them, 4-amino-2,3,5,6-tetrahalogenozenzonitrile is used particularly advantageously. The halogen atoms considered herein may be individually identical or not identical with one another and may be each a fluorine atom, chlorine atom, or bromine atom. In all the possible species of 4-amino-2,3,5, 6-tetrahalogenobenzonitrile, 4-amino-2,3,5,6-tetrafluorobenzonitrile having fluorine atoms as the halogen atoms is used particularly advantageously.

When the aromatic cyano compound mentioned above is hydrolyzed and decarboxylated in this invention, the reaction thereof is carried out in the presence of an acidic substance to produce the aromatic compound represented by the general formula (2).

The acidic substance to be used in this reaction does not need to be particularly discriminated, but is only required to be capable of hydrolyzing and decarboxylating the aromatic cyano compound represented by the general formula (1) and consequently forming the aromatic compound represented by the general formula (2). As typical examples of the acidic substance, inorganic acids such as sulfuric acid, hydrochloric acid, and nitric acid and organic acids such as acetic acid, propionic acid, and butyric acid may be cited. Among them, sulfuric acid is used particularly advantageously. The reason for this preference of sulfuric acid is that the reactivity with fluorine atoms is lowered and the reactions of the step (1) and the step (5) are enabled to proceed faster than the reactions of the step (4) and the step (8) because the amino group of the aromatic cyano compound forms a sulfate.

As the reaction vessel in the method of production according to this invention, the reaction vessel which is made of iron or stainless steel and is popularly adopted may be used. When this reaction vessel is liable to be corroded by the acidic substance or by a secondary product which occurs in the process of the reaction as when sulfuric acid is used, for example, the use of a reaction vessel made of glass or lined with glass is commendable. Otherwise, a reaction vessel which is coated with such a corrosion-resistant material as fluorocarbon resin may be used. In consideration of such factors as cost, it is common to use a reaction vessel which is made of glass or lined with glass.

The acidic substance is used together with water of an amount enough for the advance of the reactions of hydrolysis and decarboxylation of the raw material aromatic cyano compound. The acidic substance so used is preferred to have a high concentration. The reason for the high concentration of the acidic substance is that even when the raw material to be used has low purity and contains impurities, the target product, 2,3,5,6-tetrahalogenoaniline, can be obtained in a high yield without inducing corrosion of the reaction vessel. The high yield of this product may be logically explained by a supposition that when the reactions of hydrolysis and decarboxylation are carried out by using an aqueous sulfuric acid solution of a comparatively high concentration, for example, the cyano group of the impurity, 2-amino-3,4,5,6-tetrahalogenobenzonitrile, is hydrolyzed fast, the electron attracting property of the cyano group is degraded, and the readily displaceable fluorine atom at the para position relative to the cyano group is rendered less susceptible of the reaction of substitution. Further, it is inferred that since the amino group which incites fluorine atoms to undergo a reaction of nucleophilic substitution forms a salt with sulfuric acid, the reactivity of nucleophilic substitution manifested on the fluorine atoms is degraded. Though this invention is not restrained by the foregoing theoretical consideration, the acidic substance is preferred to be used in the form of an aqueous solution. The concentration of the acidic substance in this aqueous solution is properly in the range of 80 to 98 weight %, preferably in the range of 82 to 96 weight %, and more preferably in the range of 84 to 94 weight %. The reason for this range is that the product acquires the characteristic properties mentioned above when the concentration is in this range. Incidentally, the concentration of the acidic substance mentioned here means the concentration of the acidic substance which exists during the charging of the reaction vessel with the raw material or during the course of the reaction.

When an aqueous solution of sulfuric acid is used as the acidic substance, for example, since the reactions represented by the following chemical formulas (5), (6), and (7) proceed as shown by the schema in consequence of the addition of the raw material compound to the reaction mixture, the water and the sulfuric acid forming the aqueous solution are consumed proportionately and the concentration of the acidic substance in the aqueous solution is changed accordingly. Thus, the concentration of sulfuric acid which is found by determining the ratio of formation of the product in the reaction solution as by means of liquid chromatography, for example, and computing the amount of water and the amount of sulfuric acid remaining in the reaction solution based on the following chemical formulas is the concentration of the acidic substance contemplated by this invention.

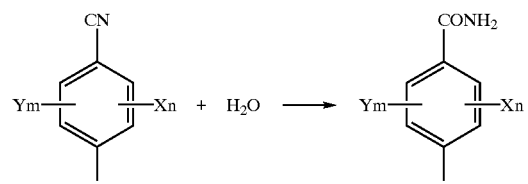

(5)

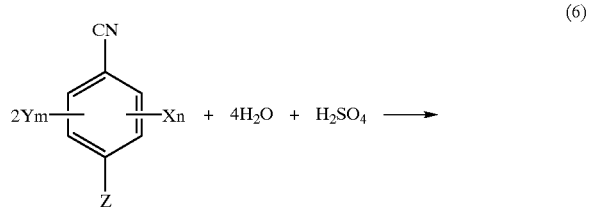

(6)

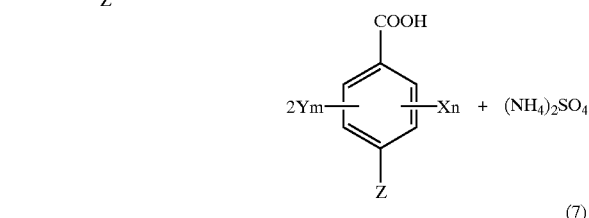

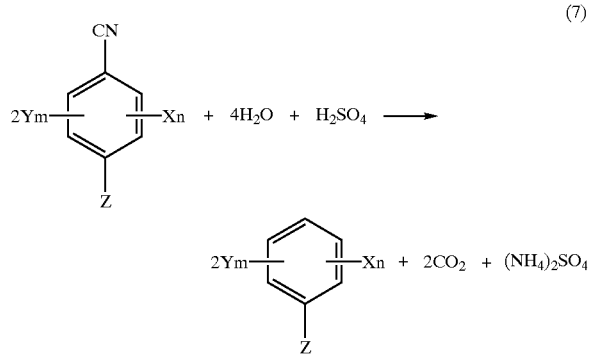

(7)

This invention is characterized by performing the reactions of hydrolysis and decarboxylation in multiple stages. In the method of this invention for the production of the aromatic compound, the reaction for hydrolyzing the CN group of the aromatic cyano compound represented by the general formula (1) into the COOH group and the reaction for decarboxylating the COOH group into the hydrogen atom proceed parallelly. The term "reactions of hydrolysis and decarboxylation" as used in this invention, therefore, is meant to express the hydrolysis and the decarboxylation collectively as a series of reactions. The expression that "the hydrolysis and the decarboxylation are performed in multiple steps," therefore, means to divide the aforementioned series of reactions into a former step in which the reactions proceed till a certain state and a latter step in which the target product is obtained at the end of the reactions. Properly, the reaction of hydrolysis is performed to a prescribed extent and thereafter, with the product of the hydrolysis left unseparated, the reaction of decarboxylation is continued under different conditions till the reactions are completed. When the reactions of hydrolysis and decarboxylation are performed in multiple stages as described above, the target product can be obtained in a high yield because the former step which is intended to effect partial hydrolysis serves to lower the reactivity of the substituent located at the para position or the ortho position with the cyano group and repress the formation of a secondary product and, particularly even when the raw material aromatic cyano compound contains impurities having halogen atoms as the component, Z, and prevent the reaction vessel from being corroded owing to the secondary production of hydrogen halogenide, and the latter step serves to complete the reactions.

The reactions of hydrolysis and decarboxylation in this invention are initiated by adding the raw material aromatic cyano compound to the reaction vessel. The reaction vessel may be charged preparatorily with the aqueous solution of the acidic substance as described above. The raw material may be added to the reaction vessel all at once, sequentially, or continuously. For this invention, the sequential addition of the raw material proves favorable in respect that it enables the selectivity of the reaction to be heightened and prevents the reaction vessel from being corroded. When the raw material is in a solid state, it may be fed to the reaction vessel in its unmodified form, or after being pulverized into a powdery state, or after being heated to a temperature higher than the melting point and consequently reduced to a molten state.

The temperature of the reactions of hydrolysis and decarboxylation is generally in the range of 50 to 180° C., preferably in the range of 60 to 160° C., and more preferably in the range of 70 to 140° C. under normal pressure. The pressure may be normal pressure, reduced pressure, or increased pressure, whichever fits the occasion best. Generally, the reactions are carried out under normal pressure or reduced pressure.

In this invention, the former step reactions are so performed that the conversion ratio of the raw material aromatic cyano compound reaches a level of not lower than 40 mol %, preferably not lower than 60 mol %, and more preferably not lower than 80 mol % and they are terminated under such conditions that the amount of the final product (the target product, which is the aromatic compound represented by the general formula (2)) to be formed is not more than 80 mol %, preferably not more than 70 mol %, and more preferably not more than 60 mol %, based on the raw material aromatic cyano compound. In other words, the reaction mixture obtained at the end of such former step reactions are enabled to contain an amide compound as the main component. Then, for the latter step reactions, the reaction conditions are so selected that the reaction of carboxylation and decarboxylation of the amide group or the reaction of decarboxylation of the carboxyl group proceeds efficiently until completion.

The reaction conditions which fulfill the conversion ratio and the amount of formation mentioned above, specifically with respect to the reaction temperature and the concentration of the acidic substance in the aqueous solution may be properly selected from the aforementioned ranges of reaction temperature and concentration of aqueous solution with respect to the contents of the reactions mentioned above. As the conditions of the former step reactions, the concentration of the acidic substance in the aqueous solution, more specifically the concentration of sulfuric acid, to be used is properly in the range of 80 to 98 weight %, preferably in the range of 82 to 96 weight %, and particularly in the range of 84 to 94 weight %. As the conditions of the latter step reactions, the concentration of the acidic substance is lowered by adding water to the reaction system to a level in the range of 50 to 95 weight %, preferably in the range of 60 to 90 weight %, and particularly in the range of 65 to 85 weight %. Specifically, the concentration of the acidic substance in the latter step is lowered from the concentration of the acidic substance in the former step by a margin in the range of 5 to 50 weight %, preferably in the range of 10 to 30 weight %. Otherwise, the reaction temperature is elevated from that of the former step by a margin in the range of 5 to 50° C., and preferably in the range of 10 to 40° C. As a result, the formation of the aromatic compound as the final product is repressed and the reaction of the raw material aromatic cyano compound is promoted by the former step reactions and the reaction of carboxylation and decarboxylation or the reaction of decaraboxylation is expedited and completed fast by the latter step reactions. In this respect, the method for the production of the aromatic compound is characterized by performing the reactions while varying the conditions of lowering the concentration of the acidic substance and/or raising the reaction temperature in the former step and the latter step in the multiple steps.

This invention is particularly effective when the raw material to be used contains as an impurity a compound having the nitrogen-containing group present in the aromatic cyano compound located at a different position. To be specific, the possibility of the aforementioned reactions by-producing the hydrogen halogenide is high when 4-amino-2,3,5,6-tetrahalogenobenzonitrile is used as the aromatic cyano compound and it contains as an impurity 2-amino-3,4,5,6-tetrahalogenobenzonitrile (o-AFBN), for example. By this invention, it is made possible to repress the secondary production of the hydrogen halogenide and preclude the occurrence of such problems as corrosion.

When 4-amino-2,3,5,6-tetrafluorobenzonitrile is used, for example, as the raw material, the conventional method necessitates a process for preparatorily purifying this raw material by such a treatment as recrystallization. By this invention, however, it is made possible to obtain the target product in a high yield without requiring such a process of purification. The 4-amino-2,3,5,6-tetrafluorobenzonitrile can be produced, for example, by causing this compound to form a diphasic state by the use of water and an organic solvent capable of forming a dibasic state with water and allowing the pentafluorobenzonitrile in the dibasic state to react with ammonia. The reaction temperature in this case is generally not higher than 70° C. As typical examples of the organic solvent, aliphatic acid esters, ketones, and benzonitriles may be cited. Thus, this invention enables the target product, i.e. the aromatic compound represented by the general formula (2), efficiently in a high yield even when the 4-amino-2,3,5,6-tetrafluorobenzonitrile containing the impurity formed by such a method is used in its unmodified form. Incidentally, the 4-amino-2,3,5,6-tetrafluorobenzonitrile formed by the method mentioned above may be used after being refined as by recrystallization to a higher degree of purify. In any event, this invention does not need to impose any limitation on the purity of 4-amino-2,3,5,6-tetrafluorobenzonitrile. Generally, so long as the purity is in the range of 80 to 100 weight %, preferably in the range of 90 to 99 weight %, the target product can be obtained efficiently without entailing such problems as the corrosion of the reaction vessel. The method of this invention is effective when the 4-amino-2,3,5,6-tetrafluorobenzonitrile which contains such an impurity as 2-amino-3,4,5,6-tetrafluorobenzonitrile and shows a purity of not higher than 97%, or not higher than 95% is used in the reaction.

Now, this invention will be described below with reference to the operation of producing 2,3,5,6-tetrafluoroaniline by using 4-amino-2,3,5,6-tetrafluorobenzonitrile as the raw material and sulfuric acid as the acidic substance.

In this invention, the reactions of hydrolysis and decarboxylation are generally fulfilled by feeding the aqueous solution of sulfuric acid to the reaction vessel made of glass or lined with glass and adding thereto 4-amino-2,3,5,6-tetrafluorobenzonitrile as the raw material. The raw material may be added to the reaction vessel all at once, or sequentially, or continuously. The sequential addition of the raw material, however, proves favorable because it gives high selectivity of the reaction and prevents the reaction vessel from corrosion. When the raw material is added sequentially, the speed of this addition may be properly selected. Favorably, this addition is made at a rate in the range of 0.1 to 20 weight parts and preferably in the range of 1 to 10 weight parts per hour, based on 100 weight parts of the aqueous solution of sulfuric acid. The addition of the raw material, 4-amino-2,3,5,6-tetrafluorobenzonitrile, is preferred to be completed prior to the termination of the former step reactions.

The sulfuric acid is used in an amount enough for permitting smooth advance of the reactions of hydrolysis and decarboxylation of 4-amino-2,3,5,6-tetrafluorobenzonitrile together with water. Generally, it is used as an aqueous sulfuric acid solution. The concentration of sulfuric acid in the aqueous sulfuric acid solution is in the range of 80 to 98 weight %, preferably in the range of 82 to 96 weight %, and more preferably in the range of 84 to 94 weight %.

The temperature of the reactions of hydrolysis and decarboxylation under normal pressure is generally in the range of 50 to 180° C., preferably in the range of 60 to 160° C., and more preferably in the range of 70 to 140° C.

The former step reactions are performed till the conversion ratio of 4-amino-2,3,5,6-tetrafluorobenzonitrile reaches a level of not lower than 40 mol %, preferably not lower than 60 mol %, and more preferably not lower than 80 mol % and are terminated when the amount of 2,3,5,6-tetrafluoroaniline formed in the reaction solution is not more than 80 mol %, preferably not more than 70 mol %, and more preferably not more than 60 mol %, based on the amount of 4-amino-2,3,5,6-tetrafluorobenzonitrile as the raw material.

Subsequently, the latter step of the process comprises adding water to the reaction mixture formed after completion of the former step reactions thereby diluting the initially charged aqueous sulfuric acid solution to a concentration in the range of 50 to 95 weight %, preferably in the range of 60 to 90 weight %, and more preferably in the range of 65 to 85 weight % and continuing the reactions on the resultant diluted reaction mixture.

Another method of this invention comprises performing the former step reactions at a comparatively low temperature, specifically a temperature in the range of 50 to 170° C., preferably in the range of 60 to 150° C., and more preferably in the range of 70 to 130° C. and performing the latter step reactions at a higher temperature than for the former step reactions, specifically at a temperature in the range of 60 to 180° C., preferably in the range of 70 to 160° C., and more preferably in the range of 80 to 140° C.

The former step reactions are performed with the concentration of the acidic acid, specifically the concentration of sulfuric acid, fixed at a level in the range of 80 to 98 weight %, preferably in the range of 82 to 96 weight %, and more preferably in the range of 84 to 94 weight % and the reaction temperature at a level in the range of 50 to 170° C., preferably in the range of 60 to 150° C., and more preferably in the range of 70 to 130° C. Subsequently the latter step reactions are performed with the concentration of the acidic substance, specifically the concentration of sulfuric acid, initially fed to the reaction vessel lowered by dilution to a level in the range of 50 to 95 weight %, preferably 60 to 90 weight % more preferably in the range of 65 to 85 weight % with a margin in the range of 5 to 50 weight %, preferably in the range of 10 to 30 weight % and the reaction temperature increased to a level in the range of 55 to 180° C., preferably in the range of 70 to 160° C. and more preferably in the range of 80 to 140° C. with a margin in the range of 5 to 50° C., preferably in the range of 10 to 40° C. As the standards for the completion of the former step reactions, the conversion ratio of 4-amino-2,3,5,6-tetraflurobenzonitril is not less than 40 mol % and the amount of formation of 2,3,5,6-tetrafluoroaniline is not more than 80 mol %. The 2,3,5,6-tetrafluoroaniline which is consequently obtained can be recovered and turned into a finished product by following the ordinary procedure.

The second aspect of this invention is the method for the production of an aromatic compound, characterized by forming an aromatic compound represented by the general formula (2) by hydrolyzing and decarboxylating an aromatic cyano compound represented by the general formula (1) in the presence of an aqueous medium and subsequently recovering the obtained aromatic compound from the reaction solution by azeotropic distillation with water.

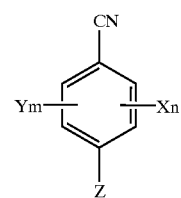

(1)

(wherein X is a halogen atom, Y is a cyano group, nitro group, or carboxyl group, Z is a nitrogen-containing group represented by —N(R$^1$)(R$^2$) (wherein R$^1$ and R$^2$ are identical or not identical substitutes superposed on a nitrogen atom and selected from among hydrogen atom and linear or branched alkyl groups of 1 to 4 carbon atoms), m is 0, 1, or 2, and n is 1, 2, 3, or 4, providing that the sum of m and n falls in the range of $1 \leq m+n \leq 4$.)

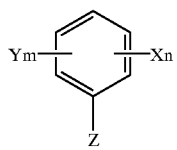

(2)

(wherein the symbols have the same meanings as in the general formula (1).)

The compound mentioned above is the same as that of the first aspect of this invention.

The second invention described above is characterized by hydrolyzing and decarboxylating the aromatic cyano compound in the presence of an aqueous medium. When the reactions are performed by using as the aqueous medium, the aqueous solution of an acidic substance such as, for example, sulfuric acid, and fixing the concentration of the acidic substance at a level of 80 weight %, the reactivity with fluorine atoms is degraded and the secondary production of hydrogen fluoride is repressed because the reactions of the step (1) and the step (5) proceed much faster than the reactions of the step (4) and the step (8) and the amino group forms a sulfate as described already in the first invention. When the aqueous medium is an alkaline substance, the target compound can be produced even with the alkaline substance. Further, by azeotropically distilling the reaction solution, the target compound can be produced in a high yield without inducing corrosion of the reaction vessel. Thus, the second aspect of this invention is enabled to produce the aromatic compound in a high yield by recovering the target compound formed in the presence of the aqueous medium by azeotropic distillation with water from the reaction solution, no matter whether the hydrolysis and the decarboxylation are effected in one step or the reactions of hydrolysis decarboxylation are effected in multiple steps, i.e. in at least not less than two steps using different reaction conditions.

The aqueous medium for use in this invention is only required to be capable of dissolving the raw material compound and may be an acidic substance or an alkaline substance. It may contain other compounds, alcohols, and aprotic polar solvents, for example.

As the aqueous medium, the acidic substance used for the first aspect of this invention may be used. As typical examples of the aqueous medium, inorganic acids such as sulfuric acid, hydrochloric acid, and nitric acid and organic acids such as acetic acid, propionic acid, and butyric acid may be cited. Among them, sulfuric acid is used particularly advantageously. First, when the aqueous medium contain an acidic substance, the concentration of the acidic substance in the aqueous medium is in the range of 80 to 98 weight %, preferably in the range of 82 to 96 weight %. The expression "concentration of the acidic substance contained in the aqueous medium" as used herein means the concentration of the acidic substance existing during the charging of the reaction vessel or during the process of the reaction.

Now, this invention will be described below with reference to one example thereof, i.e. the procedure wherein the aqueous medium is an acidic substance, sulfuric acid is used as the acidic substance, and 4-amin-2,3,5,6-tetrafluorobenzonitrile is used as the raw material compound.

This invention can be extensively applied to reaction solutions which contain aromatic compounds of the general formula (2) formed by hydrolyzing and decarboxylating aromatic cyano compounds represented by the general formula (1) under the condition having sulfuric acid containing at a concentration in the range of 80 to 98 weight %.

When the reactions use sulfuric acid, the reaction vessel in popular use which is made of glass or lined with glass is adopted. A reaction vessel which is coated as with a fluorocarbon resin may be used instead.

The reaction vessel is preparatorily charged with an aqueous sulfuric acid solution containing sulfuric acid at a concentration in the range of 80 to 98 weight %, preferably in the range of 82 to 96 weight %, and more preferably in the range of 84 to 94 weight %. If the concentration of the aqueous sulfuric acid solution to be used falls short of 80 weight %, the shortage will be at a disadvantage in not only degrading the reaction speed but also inducing corrosion of the reaction vessel. If it exceeds 98 weight %, the excess will be at a disadvantage in decreasing the speed of the formation of 4-amino-2,3,5,6-tetrafluorobenzoic acid which is the precursor of 2,3,5,6-tetrafluoroaniline and consequently lowering the speed of the formation of 2,3,5,6-tetrafluoroaniline.

The reaction temperature is in the range of 50 to 180° C., preferably in the range of 60 to 170° C., and more preferably in the range of 70 to 160° C. If this temperature falls short of 50° C., the shortage will be at a disadvantage in lowering the speed of the reaction. Conversely, if the temperature exceeds 180° C., the excess will be at a disadvantage in lowering the selectivity of the reaction.

The reactions of hydrolysis and decarboxylation are generally carried out by charging the reaction vessel with the aqueous sulfuric acid solution and adding thereto the raw material, i.e. 4-amino-2,3,5,6-tetrafluorobenzonitrile. The addition of the raw material may be made all at once or sequentially. The sequential addition of the raw material is favorable because the reactions enjoy high selectivity and the reaction vessel is prevented from corrosion. When the raw material is sequentially added, the speed of the addition may be properly selected. Favorably, this addition is made at a rate in the range of 0.1 to 20 weight parts, preferably in the range of 1 to 10 weight parts, per hour based on 100 weight parts of the charged aqueous sulfuric acid solution.

The expression "forming an aromatic compound represented by the general formula (2) by hydrolyzing and decarboxylating an aromatic cyano compound represented by the general formula (1) in the presence of an aqueous medium and subsequently" as used herein means that the molar ratio of the aromatic compound formed in the reaction vessel is not less than 85 mol %, preferably 90 mol %, and particularly preferably 95 mol %, based on the initial amount of the aromatic cyano compound represented by the formula (1). If the molar ratio falls short of 85 mol %, the shortage will be at a disadvantage in inducing the reaction vessel made of glass to sustain corrosion. After the aromatic compound represented by the general formula (2) has been formed, the product can be distilled with water azeotropically.

Favorably, the concentration of the acid substance in the aqueous medium prior to the azeotropic distillation is adjusted, as occasion demands, to a level falling short of 58 weight %, further to not more than 50 weight %, and further to not more than 40 weight %. Specifically, the adjustment of the concentration to the range mentioned above is favorably attained by using water.

When the aqueous medium is an alkaline substance, it suffices to have the concentration of the alkaline substance in the aqueous medium adjusted to a level within the range mentioned above. The adjustment of the concentration to the range mentioned above may be attained by incorporating into the aqueous medium a dilute acidic substance or alkaline substance in an amount enough for the adjustment.

Then, the azeotropic distillation which characterizes the present invention will be explained below.

From the reaction solution which is obtained as described above, the formed 2,3,5,6-tetrafluoroaniline is recovered by azeotropic distillation with water. In this case, the azeotropic distillation may be carried out after the reaction solution obtained in the presence of the aqueous medium has been mixed with water. The mixing of the reaction solution with water may be attained by adding water to the reaction solution, adding the reaction solution to a separate reaction vessel which has been charged in advance with water, or adding part of water to the reaction solution and feeding the resultant mixture to a separate reaction vessel. Generally, a method which comprises retaining the temperature of the water fed to a separate reaction vessel at a prescribed level and thereafter adding the reaction solution dropwise into the water is favorably adopted. As the aqueous medium, water or a mixture of water with an organic solvent miscible with water may be used. The use of water as the aqueous medium proves economical and advantageous in the sense that the azeotropic distillation can be performed under a favorable condition.

The amount of the water to be used for the mixing mentioned above is in the range of 0.1 to 10 weight parts, preferably in the range of 0.2 to 5 weight parts, and more preferably in the range of 0.3 to 3 weight parts, based on one weight part of the reaction solution. Generally, the water is preparatorily placed in a necessary amount collectively in a separate reaction vessel. After the azeotropic distillation has been started, the distillate is divided into water and 2,3,5,6-tetrafluoroaniline and the water expelled by this distillation is circulated to the reaction solution.

The azeotropic distillation is carried out with the temperature of the distillate in the reaction vessel (the so-called azeotropic temperature) fixed at a level in the range of 80 to 150° C., preferably in the range of 90 to 130° C. Though the pressure proper for this distillation may be either normal pressure or reduced pressure, the normal pressure proves more favorable.

The azeotropic distillation performed as described above can be likewise applied to the reaction solution which is obtained in and after the latter step of the process of the first aspect of this invention.

Now, this invention will be described below with reference to one example thereof, i.e. the procedure wherein the aqueous medium contains an alkaline substance, 4-amino-2,3,5,6-tetrafluorobenzonitrile is used as the aromatic cyano compound represented by the general formula (1), and 2,3,5,6-tetrafluoroaniline is produced as the aromatic compound represented by the general formula (2).

This invention concerns a process which comprises a step of hydrolyzing 4-amino-2,3,5,6-tetrafluorobenzonitrile under a condition containing an alkaline substance as the aqueous medium thereby obtaining 4-amino-2,3,5,6-tetrafluorobenzoic acid and/or a salt thereof (such as, for example, a sodium salt when the alkaline substance is sodium hydroxide) (hereinafter, indicated as 4-amino-2,3,5,6-tetrafluorobenzoic acid (salt)), a step of decarboxylating the compound by the reaction of decarboxylation, and finally a step of recovering the formed 2,3,5,6-tetrafluoroaniline by azeotropic distillation with water.

The alkaline substance to be used in the step for hydrolysis mentioned above does not need to be particularly discriminated but is only required to be capable of hydrolyzing 4-amino-2,3,5,6-tetrafluorobenzonitrile and consequently forming 4-amino-2,3,5,6-tetrafluorobenzoic acid (salt). Alkali metal salts, alkaline earth metal salts, and amines, for example, may be used as the alkaline substance. As concrete examples of the alkali metal salts, sodium hydroxide, potassium hydroxide, sodium carbonate, potassium carbonate, sodium hydrogen carbonate, and potassium hydrogen carbonate may be cited. As concrete examples of the alkaline earth metal salts, calcium hydroxide and calcium carbonate may be cited. The use of sodium hydroxide, among them, proves particularly advantageous by reason of economy. The combined use of sodium hydroxide and calcium hydroxide proves favorable from the viewpoint of preventing the reaction vessel from corrosion. As concrete examples of the amines, alkyl amines such as dimethyl amine, trimethyl amine, ethyl amine, diethyl amine, triethyl amine, butyl amine, dibutyl amine, and tributyl amine and pyridine and quinoline may be cited. These alkaline substances may be used either singly or in the form of a combination of two or more members.

The amount of the alkaline substance to be used is in the range of 0.1 to 20 weight parts, preferably in the range of 0.3 to 10 weight parts, and more preferably in the range of 0.5 to 5 weight parts, based on one weight part of the raw material, 4-amino-2,3,5,6-tetrafluorobenzonitrile. If the amount of the alkaline substance to be used is excessive, the excess will be at a disadvantage in inducing the raw material to undergo a reaction for halogen substitution and lowering the selectivity of the reactions. If the amount is unduly small, the shortage will be at a disadvantage in preventing the reactions from proceeding smoothly.

The reaction of hydrolysis is properly carried out in an aqueous medium. As the aqueous medium, water may be used alone or in combination with a solvent miscible with water. As the solvent of this nature, alcohols, aprotic polar solvents, ketones, and esters can be used. As concrete examples of the alcohols, methanol, ethanol, n-propanol, isopropanol, ethylene glycol, and propylene glycol may be cited. As concrete examples of ketones, acetone, methylethyl ketone, and methyl isobutyl ketone may be cited. As concrete examples of esters, acetic esters such as ethyl acetate, propyl acetate, and butyl acetate may be cited. As concrete examples of aprotic polar solvents, dimethyl formamide (DMF), dimethyl sulfoxide (DMSO), and n-methyl pyrrolidone may be cited.

The amount of the aqueous medium to be used is in the range of 1 to 50 weight parts, preferably in the range of 2 to 30 weight parts, and more preferably in the range of 3 to 10 weight parts, based on one weight part of the raw material, 4-amino-2,3,5,6-tetrafluorobenzonitrile. If this amount is unduly large, the excess will be at a disadvantage in degrading the productivity of the target compound. If the amount is unduly small, the shortage will be at a disadvantage in preventing the reactions from advancing smoothly.

The reaction temperature is in the range of 20 to 200° C., preferably in the range of 30 to 150° C., and more preferably in the range of 40 to 100° C. If the reaction temperature is excessively high, the excess will be at a disadvantage in increasing secondary products due to the reaction of halogen substitution of the raw material and consequently lowering the selectivity of the target compound. Conversely, if the reaction temperature is excessively low, the shortage will beat a disadvantage in preventing the reactions from advancing at an economically sufficient speed.

The present process, because of the use of an alkaline substance, conspicuously allays the corrosion of the reaction vessel as compared with the conventional process which uses an acidic substance.

Now, the step of decarboxylaion will be explained below. This is the step of performing the reaction of decarboxylation of the 4-amino-2,3,5,6-tetrafluorobenzoic acid (salt) formed by the reaction of hydrolysis.

The reaction of decarboxylation may be attained by directly heating the aqueous medium containing the 4-amino-2,3,5,6-tetraflurobenzoic acid (salt) formed by the reaction of hydrolysis. It may be otherwise fulfilled by adding for the reactions an alkaline substance different from the alkaline substance used at the step of hydrolysis. As concrete examples of the alkaline substance proper for the addition, those alkaline substances enumerated above may be cited. Among other alkaline substances mentioned above, the alkaline earth metal salts prove advantageous because they allow the reactions to proceed more smoothly and prevent the reaction vessel from being corroded with the fluorine ions formed by the secondary reaction involved in the step of decarboxylation. The amount of the alkaline earth metal salt to be used is in the range of 0.01 to 2 weight parts, preferably in the range of 0.02 to 1 weight part, and more preferably in the range of 0.03 to 0.5 weight part, based on one weight part of the 4-amino-2,3,5,6-tetrafluorobenzoic acid (salt). If the amount so used is unduly large, the excess will be at a disadvantage in increasing the secondary produces due to the reaction of halogen substitution of the raw material and consequently lowering the selectivity of the target compound. Conversely, if this amount is unduly small, the shortage will be at a disadvantage in precluding fulfillment of the effect mentioned above.

The decarboxylation may be effected after the alkaline substance existing in the aqueous medium has been partially or completely neutralized by the addition of an acidic substance to the aqueous medium.

The acidic substance mentioned above may be either an inorganic acid or an organic acid. As concrete examples of the inorganic acid, hydrochloric acid, sulfuric acid, and nitric acid may be cited. As concrete examples of the organic acid, formic acid, acetic acid, propionic acid, and butyric acid may be cited. By reason of economy, sulfuric acid is used particularly favorably among them. The amount of the acidic substance to be used is in the range of 0.1 to 2 equivalents, preferably in the range of 0.3 to 1.5 equivalents, and more preferably in the range of 0.5 to 1 equivalent, based on the weight of the alkaline substance. If this amount is unduly small, the shortage will be at a disadvantage in preventing the target compound from being obtained at a sufficiently high speed of reaction. conversely, if the amount is unduly large, the excess will be at a disadvantage in compelling the reaction of decarboxylation to proceed under an acidic condition, increasing the secondary products due to the reaction of halogen substitution of the raw material, and consequently inducing corrosion of the reaction vessel due to the generation of hydrogen fluoride.

The reaction of decarboxylation may be performed under either normal pressure or increased pressure. Favorably, it is carried out under increased pressure such as, for example, a pressure in the approximate range of 0.1 to 5 MPa because the reactions proceed more smoothly under the increased pressure. When the reactions are performed under the increased pressure, they may be effected by using a pressure-resistant reaction vessel and keeping a closed system therein by accumulating a gas in the reaction vessel. The reactions may be otherwise carried out by partially extracting from the reaction vessel the gas having as its main component the carbon dioxide gas generated by the reactions thereby keeping the pressure in the reaction vessel at a fixed level.

The reaction temperature is in the range of 30 to 200° C., preferably in the range of 50 to 180° C., and more preferably in the range of 70 to 160° C. If the reaction temperature is unduly high, the excess will be at a disadvantage in increasing the secondary products due to the reaction of halogen substitution of the raw material and consequently entailing such problems as corrosion of the reaction vessel due to the generation of hydrogen fluoride. Conversely, if the reaction temperature is unduly low, the shortage will be at a disadvantage in preventing the reactions from proceeding smoothly.

The step of hydrolysis and the step of decarboxylation mentioned above may be performed in one and the same reaction vessel or indifferent reaction vessel. As the reaction vessel, the reaction vessel in common use which is made of carbon steel or stainless steel may be used.

The molar ratio of the aromatic compound to be formed in the reaction vessel engaging in azeotropic distillation, similarly to the reactions using an aqueous solution as an acidic substance, means that the molar ratio of the aromatic compound of the general formula (2) to be formed reaches a level of not less than 85 mol %, preferably 90 mol %, and more preferably 95 mol %, based on the initial amount of the aromatic cyano compound represented by the formula (1). The step of azeotropic distillation is the same as when the acidic substance is used.

The third aspect of this invention is in the production of an aromatic compound represented by the general formula (2) by hydrolyzing and decarboxylating an aromatic cyano compound represented by the general formula (1) in the presence of an acidic substance, a method for the production of the aromatic compound, characterized by performing the hydrolysis and decarboxylation in multiple steps and effecting the recovery of the formed aromatic compound from the reaction solution by azeotropic distillation with water.

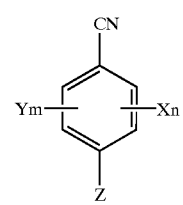

(1)

(wherein X is a halogen atom, Y is a cyano group, nitro group, or carboxyl group, Z is a nitrogen-containing group represented by —N(R$^1$)(R$^2$) (wherein R$^1$ and R$^2$ are identical or not identical substitutes superposed on a nitrogen atom and selected from among hydrogen atom and linear or branched alkyl groups of 1 to 4 carbon atoms), m is 0, 1, or 2, and n is 1, 2, 3, or 4, providing that the sum of m and n falls in the range of $1 \leq m+n \leq 4$.)

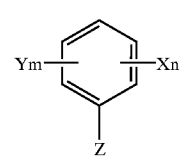

(2)

(wherein the symbols have the same meanings as in the general formula (1).)

The third invention is directed to a process which comprises hydrolyzing and decarboxylating the aromatic cyano compound represented by the general formula (1) in multiple steps including a former step and a latter step using different reaction conditions in the presence of the acidic substance thereby producing the aromatic compound represented by the general formula (2) and subsequently recovering the formed aromatic compound from the reaction solution by azeotropic distillation with water. Since the reactions are performed in at least two steps by using the acidic substance, the secondary production of such a corrosive substance as hydrofluoric acid can be repressed. Further, since the target compound is recovered by azeotropy, it is made possible to prevent the reaction vessel from being corroded during the course of the azeotropy and enable the target compound to be produced in a high yield.

The compounds represented by the general formulas (1) and (2) mentioned above are the same as those of the first aspect of this invention. Further, the "acidic substance" to be used and the conditions for performing "the reactions of hydrolysis and decarboxylation in multiple steps including a former step and a latter step using different reaction conditions" are the same as those which have been covered in the foregoing description of the first aspect of the invention. In the present invention, the molar ratio of the aromatic compound of the formula (2) formed in the reaction vessel is not less than 85 mol %, preferably 90 mol %, and more preferably 95 mol %, based on the initial amount of the aromatic cyano compound represented by the formula (1). If this molar ratio falls short of 85 mol %, the shortage will be at a disadvantage in inducing the reaction vessel of glass used for the reactions of hydrolysis and decarboxylation or in the step of azeotropy to sustain corrosion. The conditions for azeotropically distilling the formed aromatic compound are the same as those which are covered by the foregoing description of the second aspect of the invention.

EXAMINATIONS

Now, this invention will be described more specifically with reference to working examples adduced hereinafter for illustration.

Referential Example 1

Synthesis of 4-amino-2,3,5,6-tetrafluorobenzonitrile

A 500 ml four-neck flask provided with a stirrer, a thermometer, and a cooling tube was charged with 75 g (389 mmols) of pentafluorobenzonitrile, 225 ml of n-propyl acetate, 79.5 g of an aqueous 25% ammonia solution (1.165 mols as ammonia), and 0.375 g of tetrabutyl ammonium bromide. The contents of the reaction vessel were left reacting at 25° C. for one hour and further reacting at 50° C. for five hours. When the reaction solution obtained after completion of the reaction was analyzed by gas chromatography, the conversion ratio of pentafluorobenzonitrile was found to be 100% and the yield of the target component, 4-amino-2,3,5,6-tetrafluorobenzonitrile to be 94%.

The n-propyl acetate layer containing 4-amino-2,3,5,6-tetrafluorobenzonitrile was separated and washed twice with 100 g of an aqueous 10 weight % sodium sulfate solution to remove the ammonium fluoride contained in the layer. Subsequently, the n-propyl acetate layer was heated to expel the n-propyl acetate by distillation and obtain 73.5 g of 4-amino-2,3,5,6-tetrafluorobenzonitrile (purity 94%) (yield 93.6%). The product contained 4.5 g (6%) of 2-amino-3,4,5,6-tetrafluorobenzonitrile as an impurity.

EXAMPLE 1

(Former Step Reactions)

A 200 ml four-neck flask made of glass and provided with a stirrer, a thermometer, and a cooling tube was charged with 120 g of an aqueous 90 weight % sulfuric acid solution and heated till the internal temperature thereof reached 110° C., with the solution kept stirred. Subsequently, 50 g of the solid obtained in Referential Example 1 (having a 4-amino-2,3,5,6-tetrafluorobenzonitrile content of 94%) was fed at a feed rate of 4 g/h to an aqueous 90 weight % sulfuric acid solution kept at 110° C. The concentration of sulfuric acid in the reaction vessel during the former step reactions was in the range of 90 to 94 weight %. After the feeding was completed, the reaction was further continued for two hours. When the reaction solution was sampled and analyzed by liquid chromatography, the conversion ratio of 4-amino-2,3,5,6-tetrafluorobenzonitrile was 100 mol % and the products formed in the reaction solution were found to be as follows.

4-Amino-2,3,5,6-tetrafluorobenzamide 65 mol %
4-Amino-2,3,5,6-tetrafluorobenzoic acid 10 mol %
2,3,5,6-Tetrafluoroaniline 20 mol %

(Latter Step Reactions)

By adding 22 g of water to the reaction solution mentioned above, the concentration of the aqueous sulfuric acid solution was adjusted to 80 weight % and the reaction was continued for 15 hours. The concentration of sulfuric acid in the reaction vessel during the latter step reactions was 80 weight %. When the reaction solution obtained after completion of the reaction was sampled and analyzed by liquid chromatography, the yield of 2,3,5,6-tetrafluoroaniline was found to be 98 mol %.

(Step of Azeotropy)

A 500 ml four-neck flask made of glass and provided with a stirrer, a thermometer, a dropping funnel, and a water separating tube was charged with 300 ml of water and heated to 100° C., with the water therein as kept stirred, to retain a state of reflux in the reaction vessel.

The reaction solution obtained in the step of hydrolysis and decarboxylation was placed in the dropping funnel, retained at 110° C. by means of an electric heater, and added dropwise into the flask over a period of one hour, and subjected to azeotropic distillation to expel 2,3,5,6-tetrafluoroaniline into the water separating tube.

The upper layer of the distillate collecting in the water separating tube was water and the lower layer thereof was 2,3,5,6-tetrafluoroaniline. The expulsion of 2,3,5,6-tetrafluoroaniline by distillation was continued for three hours, with the distilled water circulated continuously into the flask.

From the water separating tube, 39.4 g of 2,3,5,6-tetrafluoroaniline was obtained. When this compound was analyzed by gas chromatography, the purity thereof was found to be 99.5%. The total yield in the step of hydrolysis and decarboxylation and the step of azeotropic distillation was found to be 96.0%. When the inner walls of the reaction vessels used for the hydrolysis and decarboxylation and for the azeotropic distillation were visually inspected, no discernible sign of corrosion was detected.

(Determination of Annual Ratio of Corrosion)

The reaction vessels used in the reactions mentioned above were measured for annual ratio of corrosion. The reactions of hydrolysis and decarboxylation were carried out by following the procedure described above while using a 500 ml separable flask made of stainless steel lined with a fluorocarbon resin in place of a flask made of glass, having a glass test piece (pestle type, made by NGK Insulators Ltd., and sold under the product code of "GL-400") immersed near the interface, and tripling the amounts of the aqueous sulfuric acid solution and the solid, and the speed of addition of the solid. This reaction was performed up to two repetitions. When the test piece which had undergone the reaction three times was taken out and tested for annual ratio of corrosion in accordance with the following formula. The ratio was found to be 0.02 mm/year.

Annual ratio of corrosion (mm/year)=$\{[(W_0-W_1)/D]/S\} \times \{[24(hr/day) \times 365(days/year)]/T\}$ wherein $W_0$: weight of test piece before the test (mg)
$W_1$: weight of test piece after the test (mg)
D: specific gravity of test piece (mg/mm$^3$)
S: surface area of test piece (mm$^2$)
T: duration of test (hr)

EXAMPLE 2
(Reactions of Hydrolysis and Decarboxylation)

A 200 ml four-neck flask made of glass and provided with a stirrer, a thermometer, and a cooling tube was charged with 100 g of an aqueous 90% sulfuric acid solution and heated till the internal temperature thereof reached 100° C., with the solution as kept stirred. Then, 50 g of the solid (having a 4-amino-2,3,5,6-tetrafluorobenzonitrile content of 94%) obtained in Referential Example 1 was fed at a feed rate of 4 g/h to an aqueous 90% sulfuric acid solution, with the solution as kept stirred. After the supply was completed, the reaction was continued further for two hours. When the reaction solution was sampled and analyzed by liquid chromatography, the conversion ratio of 4-amino-2,3,5,6-tetrafluorobenzonitrile was found to be 98 mol % and the products formed in the reaction solution were found to be as follows.

4-Amino-2,3,5,6-tetrafluorobenzamide 55 mol %
4-Amino-2,3,5,6-tetrafluorobenzoic acid 10 mol %
2,3,5,6-Tetrafluoroaniline 8 mol %

The concentration of the aqueous sulfuric acid solution was adjusted to 80% by adding 19 g of water to the reaction solution and also heated to 120° C. The ensuing reaction was continued for 15 hours. When the reaction solution obtained after completion of the reaction was sampled and analyzed by liquid chromatography, the yield of 2,3,5,6-tetrafluoroaniline was found to be 98%.

(Step of Azeotropy)

A 500 ml four-neck flask made of glass and provided with a stirrer, a thermometer, a dropping funnel, and a water separating tube was charged with 300 ml of water and heated to 100° C., with the water as kept stirred, to retain a state of reflux in the flask.

The reaction solution obtained in the step of hydrolysis and decarboxylation was placed in the dropping funnel, retained at 110° C. by means of an electric heater, and added drop wise into the flask over a period of one hour, and subjected to azeotropic distillation to expel 2,3,5,6-tetrafluoroaniline into the water separating tube.

The upper layer of the distillate collecting in the water separating tube was water and the lower layer thereof was 2,3,5,6-tetrafluoroaniline. The expulsion of 2,3,5,6-tetrafluoroaniline by distillation was continued for three hours, with the distilled water circulated continuously into the flask.

From the water separating tube, 39.7 g of 2,3,5,6-tetrafluoroaniline was obtained. When this compound was analyzed by gas chromatography, the purity thereof was found to be 99.8%.

The total yield in the step of hydrolysis and decarboxylation and the step of azeotropic distillation was found to be 97.1%. When the inner walls of the reaction vessels used for the hydrolysis and decarboxylation and for the azeotropic distillation was visually inspected, no discernible sign of corrosion was detected.

(Determination of Annual Ratio of Corrosion)

When the reaction vessels used in the reaction of hydrolysis and the reaction of decarboxylation were measured for annual ratio of corrosion by following the procedure of Eample 1, the ratio was found to be 0.03 mm/year.

EXAMPLES 3 to 8

The hydrolysis and decarboxylation and the azeotropic distillation were performed by following the procedure of Example 1 while changing the concentrations of sulfuric acid, the reaction temperatures, and the duration of reaction in the former step reactions and the latter step reactions as shown in Table 1. The conversion ratio of the raw material (4-amino-2,3,5,6-tetrafluorobenzonitrile), the amount of TFA (2,3,5,6-tetrafluoroaniline) formed (mol %), the presence or absence of corrosion on the reaction vessels used for the reaction of analysis and the reaction of decarboxylation, the yields (yields at the steps of hydrolyxis and decarboxylation), and the annual ratio of corrosion were as shown in Table 1. The results of Examples 1 and 2 are collectively shown in the table 1.

TABLE 1

| | Former step reactions | | | | | Former step reactions | | | | | Annual corrosion ratio (mm/year) |
|---|---|---|---|---|---|---|---|---|---|---|---|
| Example | Temp. (° C.) | Conc. of $H_2SO_4$ (%) | Duration (hr) | conversion ratio (mol %) | Amount of TFA (mol %) | Temp. (° C.) | Conc. of $H_2SO_4$ (%) | Duration (hr) | Yield of TFA (mol %) | Corrosion (determined) | |
| 1 | 110 | 90 | 15 | 100 | 20 | 110 | 80 | 15 | 98 | none | 0.02 |
| 2 | 100 | 90 | 15 | 98 | 8 | 120 | 80 | 15 | 98 | none | 0.03 |
| 3 | 90 | 95 | 17 | 95 | 7 | 110 | 80 | 16 | 97 | none | 0.01 |
| 4 | 100 | 90 | 18 | 100 | 8 | 120 | 90 | 14 | 98 | none | 0.03 |
| 5 | 120 | 90 | 13 | 100 | 31 | 120 | 80 | 8 | 97 | none | 0.05 |
| 6 | 110 | 85 | 16 | 100 | 25 | 120 | 85 | 10 | 99 | none | 0.04 |
| 7 | 80 | 95 | 12 | 90 | 3 | 120 | 85 | 20 | 98 | none | 0.02 |
| 8 | 70 | 95 | 15 | 85 | 2 | 110 | 80 | 21 | 97 | none | 0.01 |
| Comparative Example 1 | 140 | 60 | 6 | 96 | 82.5 | — | — | — | — | found | 0.30 |

EXAMPLE 9
(Step of Hydrolysis and Decarboxylation)

A 200 ml four-neck flask provided with a stirrer, a thermometer, and a cooling tube was charged with 120 g of an aqueous 85% sulfuric acid solution, heated to 130° C., and thereafter retained at this temperature. Into the flask, 40 g of the 4-amino-2,3,5,6-tetrafluorobenzonitrile (94% in purity) obtained in Referential Example 1 was added in a molten state dropwise at a rate of 4 g/h over a period of 10 hours. After the dropwise addition was completed, the reaction was further continued for eight hours. When the reaction solution obtained at the end of the reaction was analyzed by liquid chromatography, the conversion ratio of 4-amino-2,3,5,6-tetrafluorobenzonitrile was found to be 100% and the yield of the target product, 2,3,5,6-tetrafluoroaniline, was found to be 98%.

(Step of Azeotropy)

In a 200 ml four-neck flask provided with a stirrer, a thermometer, a dropping funnel, and a water separating tube, 50 g of water was placed, heated to 100° C., and retained at this temperature. Then, the reaction solution obtained at the steps mentioned above was transferred into the dropping funnel adapted to retain temperature by heating and dropped therefrom at a rate of 120 g/hr. The temperature of heating in the reaction vessel was continuously elevated so as to expel the target product, 2,3,5,6-tetrafluoroaniline by distillation into the water separating tube at 100° C. during the initial stage of the distillation and at 140° C. at the time of completion of the distillation. The 2,3,5,6-tetrafluoroaniline expelled by distillation was withdrawn into a receptacle and the water formed by distillation was returned to the four-neck flask. Thus the expulsion of 2,3,5,6-tetrafluoroaniline by distillation was continued for three hours. As a result, 32 g of 2,3,5,6-tetra fluoroaniline having a purity of 98.5% was obtained. The yield was 98.5%.

When the inner walls of the reaction vessels used for the hydrolysis and the decarboxylation and for the azeotropic distillation were visually inspected, no discernible sign of corrosion was detected on any of the reaction vessels. When the reaction vessels used for the hydrolysis and the decarboxylation were measured for annual ratio of corrosion, the ratio was found to be 0.09 mm/year.

Comparative Example 1

2,3,5,6-Tetrafluoroaniline was produced from 4-amino-2,3,5,6-tetrafluorobenzonitrile. To be specific, in a 200 ml four-neck flask provided with a stirrer, a thermometer, a dropping funnel, and a water separating tube, 100 g of 60% sulfuric acid was placed and heated to 140° C. To the hot sulfuric acid, 36 g of the raw material, 4-amino-2,3,5,6-tetrafluorobenzonitrile (having a purity of 94% and containing 6% of 2-amino-3,4,5,6-tetrafluorobenzonitrile as an impurity) was added dropwise at a rate of 6 g/hr. The 2,3,5,6-tetrafluoroaniline which was formed by the reaction was expelled by azeotropy with water, guided into the water dropping tube, and separated from the water. The reaction was continued for six hours while the reaction vessel was supplied with the same amount of water as expelled by distillation. After the completion of the reaction, the conversion ratio of the raw material determined by gas chromatography was found to be 96 mol %. When the 2,3,5,6-tetrafluoroaniline expelled by distillation was analyzed, the purity was found to be 95.3% and the yield to be 82.5%.

When the reaction vessels were visually inspected, the inner walls thereof were found to sustain a discernible corrosion probably induced by hydrogen fluoride. The annual ratio of corrosion was 0.3 mm/year.

EXAMPLE 10

(Step of Hydrolysis)

In a 100 ml four-neck flask provided with a stirrer, a thermometer, and a cooling tube, 14.7 g of the solid (having a 4-amino-2,3,5,6-tetrafluorobenzonitrile content of 94%) obtained in Referential Example 1 was placed and 80 g of an aqueous 10% sodium hydroxide solution was further added thereto and they were allowed to react at 50° C. for eight hours. When the reaction solution obtained at the end of the reaction was analyzed by gas chromatography, the conversion ratio of 4-amino-2,3,5,6-tetrafluorobenzonitrile was found to be 100% and the yield of the target compound, 4-amino-2,3,5,6-tetrafluorobenzoic acid, was found to be 98%.

(Step of Decarboxylation)

A 100 ml autoclave was charged with the reaction solution obtained in the step of hydrolysis plus 9.8 g of concentrated sulfuric acid (equivalent to the sodium hydroxide used in the step of hydrolysis). With the inner temperature of the autoclave elevated to 130° C. and the inner pressure of the reaction vessel retained at 0.2 MPa, the reaction was carried out for eight hours. When the reaction solution obtained after the completion of the reaction was analyzed by gas chromatography, the conversion ratio of 4-amino-2,3,5,6-tetrafluorobenzoic acid was found to be 100% and the yield of 2,3,5,6-tetrafluoroaniline was found to be 95%.

(Step of Azeotropy)

In a 200 ml four-neck flask provided with a stirrer, a thermometer, a dropping funnel, and a water separating tube, the reaction solution obtained in the step of decarboxylation was placed, heated to 100° C. and retained at this temperature. With the water placed in the dropping funnel added dropwise thereto, the temperature of the heating of the flask was elevated so as to expel the target compound, 2,3,5,6-tetrafluoroaniline by distillation into the water separation tube. The expulsion of 2,3,5,6-tetrafluoroaniline by distillation was attained at 100° C. in a reaction vessel during the initial stage of distillation and at 140° C. at the time of completing the distillation.

With the distilled 2,3,5,6-tetrafluoroaniline withdrawn into a receptacle and the distilled water returned to the four-neck flack, the expulsion of 2,3,5,6-tetrafluoroaniline by distillation was continued for three hours. As a result, 11.3 g of 2,3,5,6-tetrafluoroaniline having a purity of 98.5% was obtained.

The total yield in the step of hydrolysis and decarboxylation and in the step of azeotropy was 94.5%. When the interiors of the reaction vessels used for the hydrolysis and the decarboxylation and for the azeotropy were visually inspected, no discernible sign of corrosion was detected in any of the reaction vessels. The annual ratio of corrosion of the reaction vessels used for the step of hydrolysis and decarboxylation was 0.02 mm/year.

What is claimed is:

1. In the production of an aromatic compound represented by the general formula (2) by hydrolyzing and decarboxylating an aromatic cyano compound represented by the general formula (1) in the presence of an acidic substance, a method for the production of the aromatic. compound, characterized by performing the reactions of hydrolysis and decarboylation in multiple steps

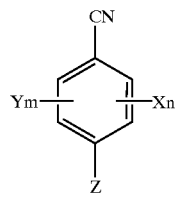

(1)

(wherein X is a halogen atom, Y is a cyano group, nitro group, or carboxyl group, Z is a nitrogen-containing group represented by —$N(R^1)(R^2)$ (wherein $R^1$ and $R^2$ are identical or not identical substitutes superposed on a nitrogen atom and selected from among hydrogen atom and linear or branched alkyl groups of 1 to 4 carbon atoms), m is 0, 1, or 2, and n is 1, 2, 3, or 4, providing that the sum of m and n falls in the range of $1 \leq m+n \leq 4$)

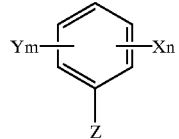

(2)

(wherein the symbols have the same meanings as in the general formula (1).

2. A method according to claim 1, wherein the conversion ratio of the aromatic cyano compound represented by the general formula (1) is fixed at a level of not less than 40 mol % and the molar ratio of the formation of the aromatic compound represented by the general formula (2) to the initial amount of the aromatic cyano compound represented by the formula (1) is fixed at a level of not more than 80 mol % in a former step reaction in said multiple steps respectively, and subsequently the reactions of hydrolysis and decarboxylation are terminated in and after a latter step reactions in said multiple steps.

3. A method according to claim 1, wherein the reactions in the former step and the latter step in said multiple steps are carried out on the conditions of lowering the concentration of said acidic substance and/or increasing the reaction temperature.

4. A method according to claim 3, wherein said acidic substance is an aqueous sulfuric acid solution.

5. A method according to claim 1, wherein said aromatic cyano compound is 4-amino-2,3,5,6-tetrahalogenobenzonitrile and said aromatic compound is 2,3,5,6-tetrahalogenoaniline.

6. A method according to claim 1, wherein said reactions of hydrolysis and decarboxylation are carried out in the presence of sulfuric acid in a reaction vessel made of glass or lined with glass.

7. A method for the production of an aromatic compound, characterized by forming an aromatic compound represented by the general formula (2) by hydrolyzing and decarboxylating an aromatic cyano compound represented by the general formula (1) in the presence of an aqueous medium and subsequently recovering the obtained aromatic compound from the reaction solution by azeotropic distillation with water

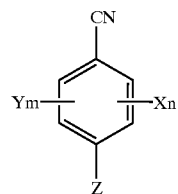

(1)

(wherein X is a halogen atom, Y is a cyano group, nitro group, or carboxyl group, Z is a nitrogen-containing group represented by —$N(R^1)(R^2)$ (wherein $R^1$ and $R^2$ are identical or not identical substitutes superposed on a nitrogen atom and selected from among hydrogen atom and linear or branched alkyl groups of 1 to 4 carbon atoms), m is 0, 1, or 2, and n is 1, 2, 3, or 4, providing that the sum of m and n falls in the range of $1 \leq m+n \leq 4$)

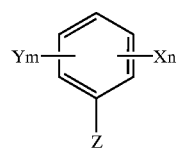

(2)

(wherein the symbols have the same meanings as in the general formula (1).

8. A method according to claim 7, wherein said aqueous medium contains an acidic substance and the concentration of the acidic substance in said aqueous medium is in the range of 80 to 98 weight %.

9. A method according to claim 8, wherein said acidic substance is sulfuric acid.

10. A method according to claim 7, wherein the molar ratio of the formation of the aromatic compound represented by the general formula (2) is not less than 85 mol % to the initial amount of the aromatic cyano compound represented by the general formula (1).

11. A method according to claim 7, wherein said aromatic cyano compound is 4-amino-2,3,5,6-tetrahalogenobenzonitrile and said aromatic compound is 2,3,5,6-tetrahalogenoaniline.

12. A method according to claim 7, wherein said aqueous medium contains an alkaline substance.

13. A method according to claim 7, wherein said aromatic cyano compound is 4-amino-2,3,5,6-tetrafluorobenzonitrile and said aromatic compound is 2,3,5,6-tetrafluoroaniline.

14. In the production of an aromatic compound represented by the general formula (2) by hydrolyzing and decarboxylating an aromatic cyano compound represented by the general formula (1) in the presence of an acidic substance, a method for the production of the aromatic compound, characterized by performing the hydrolysis and decarboxylation in multiple steps and effecting the recovery of the formed aromatic compound from the reaction solution by azeotropic distillation with water

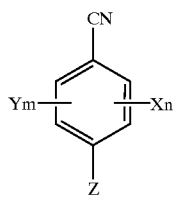

(1)

(wherein X is a halogen atom, Y is a cyano group, nitro group, or carboxyl group, Z is a nitrogen-containing group represented by $-N(R^1)(R^2)$ (wherein $R^1$ and $R^2$ are identical or not identical substitutes superposed on a nitrogen atom and selected from among hydrogen atom and linear or branched alkyl groups of 1 to 4 carbon atoms), m is 0, 1, or 2, and n is 1, 2, 3, or 4, providing that the sum of m and n falls in the range of $1 \leq m+n \leq 4$)

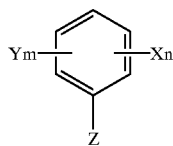

(2)

(wherein the symbols have the same meanings as in the general formula (1).

15. A method according to claim 14, wherein a former step reactions in said multiple steps are carried out under the condition of an acidic state in a concentration in the range of 80 to 98 weight % to react an aromatic cyano compound represented by the general formula (1) and subsequently a latter step reactions in said multiple steps are carried out under the condition of having the concentration of said acidic substance lowered by a level in the range of 5 to 50 weight % and/or elevating the reaction temperature by a level in the range of 5 to 30° C.

16. A method according to claim 14, wherein the molar ratio of the formation of the aromatic compound represented by the formula (2) to the aromatic cyano compound represented by the formula (1) in said reaction solution is not less than 85 mol %.

17. A method according to claim 14, wherein said acidic substance is an aqueous sulfuric acid solution.

* * * * *